(12) United States Patent
Colaizzi

(10) Patent No.: US 11,744,505 B2
(45) Date of Patent: Sep. 5, 2023

(54) TRAUMATIC BRAIN INJURY DIAGNOSTICS SYSTEM AND METHOD

(71) Applicant: Tristan Alan Colaizzi, Alexandria, VA (US)

(72) Inventor: Tristan Alan Colaizzi, Alexandria, VA (US)

(*) Notice: Subject to any disclaimer, the term of this patent is extended or adjusted under 35 U.S.C. 154(b) by 420 days.

(21) Appl. No.: 16/839,637

(22) Filed: Apr. 3, 2020

(65) Prior Publication Data

US 2020/0315516 A1 Oct. 8, 2020

Related U.S. Application Data

(60) Provisional application No. 62/829,462, filed on Apr. 4, 2019.

(51) Int. Cl.
*A61B 5/00* (2006.01)
*A61B 5/024* (2006.01)
*G16H 10/60* (2018.01)

(52) U.S. Cl.
CPC ........ *A61B 5/4064* (2013.01); *A61B 5/02405* (2013.01); *A61B 5/6802* (2013.01); *A61B 5/7275* (2013.01); *A61B 5/746* (2013.01); *G16H 10/60* (2018.01); *A61B 2562/02* (2013.01)

(58) Field of Classification Search
CPC . A61B 5/4064; A61B 5/02405; A61B 5/6802; A61B 5/7275; A61B 5/746; A61B 2562/02; G16H 10/60
See application file for complete search history.

(56) References Cited

U.S. PATENT DOCUMENTS

| | | | |
|---|---|---|---|
| 2005/0251051 A1* | 11/2005 | Pougatchev | ....... A61B 5/02405 600/509 |
| 2010/0174205 A1* | 7/2010 | Wegerif | ............. A61B 5/02405 600/515 |
| 2011/0282169 A1 | 11/2011 | Grudic et al. | |
| 2012/0123232 A1* | 5/2012 | Najarian | .................. G16Z 99/00 600/407 |
| 2016/0051179 A1* | 2/2016 | Herman | ............. A61B 5/02405 600/479 |
| 2018/0250510 A1* | 9/2018 | Ziv | ....................... A61B 5/0245 |
| 2019/0000349 A1 | 1/2019 | Narayan et al. | |

FOREIGN PATENT DOCUMENTS

| | | | | |
|---|---|---|---|---|
| WO | WO-2011130541 A2 * | 10/2011 | .......... | A61B 5/0006 |
| WO | 2016110804 A1 | 7/2016 | | |

OTHER PUBLICATIONS

International Search Report and Written Opinion issued in related International Patent Application No. PCT/US2020/026687 dated Jun. 16, 2020.

* cited by examiner

*Primary Examiner* — Nabil H Syed
*Assistant Examiner* — Cal J Eustaquio
(74) *Attorney, Agent, or Firm* — Michele V. Frank; Venable LLP

(57) ABSTRACT

According to an embodiment, a method for diagnosing traumatic brain injury (TBI) in a subject may include repeatedly measuring heart rate variability (HRV) in the subject and a plurality of HRV altering variables; calculating an HRV fingerprint based on the subject's measured HRV and the measured plurality of HRV altering variables; generating a predicted HRV of the subject based on the HRV fingerprint; and diagnosing a TBI in the subject when the measured HRV of the subject deviates from the predicted HRV of the subject.

20 Claims, 9 Drawing Sheets

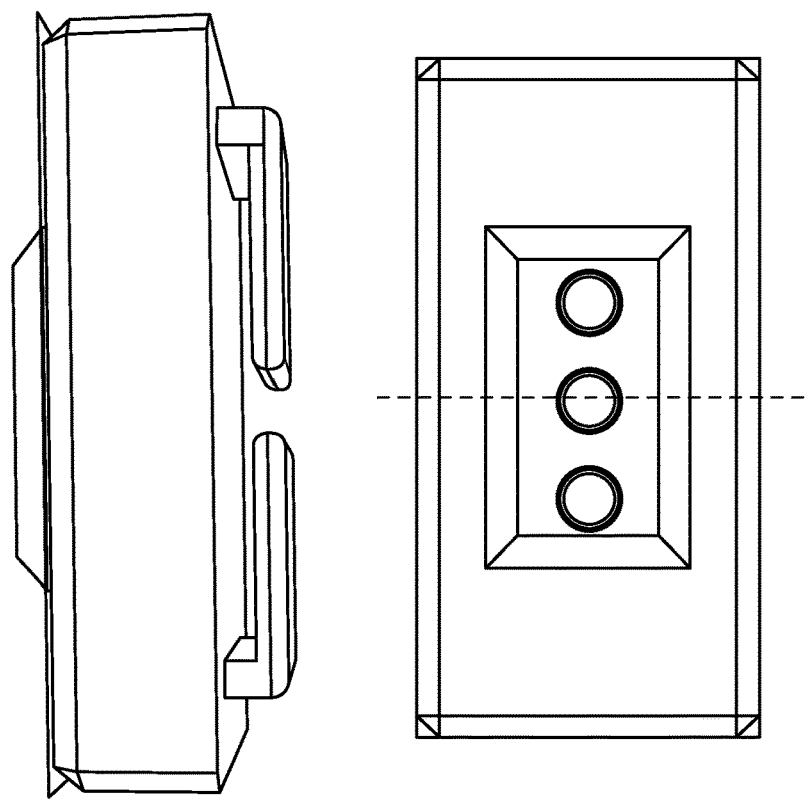
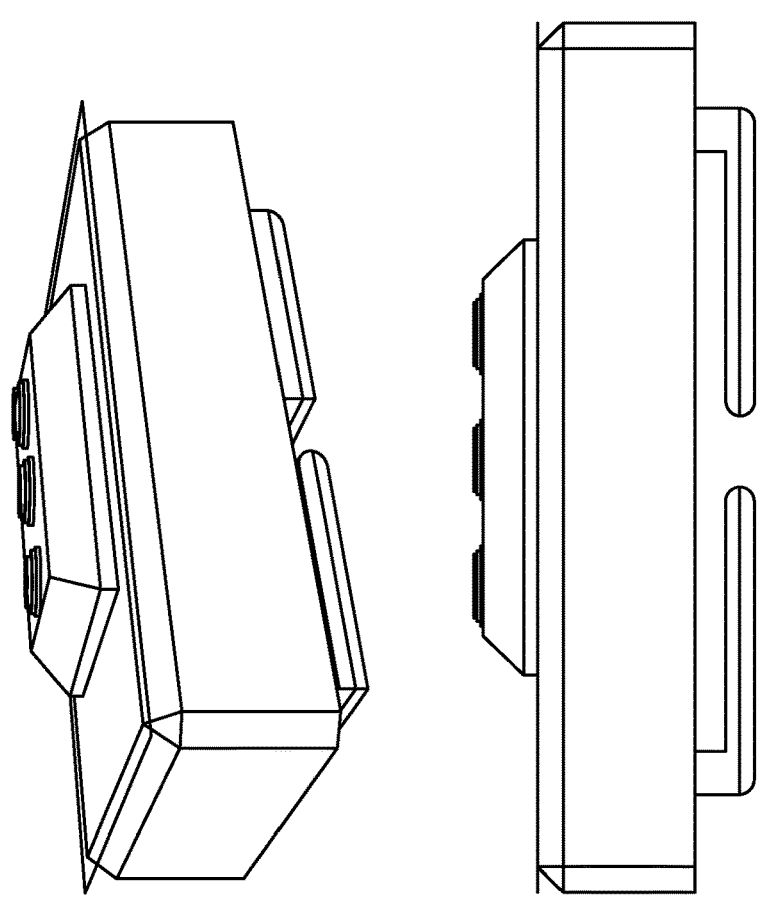
FIG. 3

| VARIABLE (UNITS) | DEFINITION | PHYSIOLOGICAL SIGNIFICANCE |
|---|---|---|
| *TIME DOMAIN* | | |
| SDNN (MS) | STANDARD DEVIATION OF INTERVALS BETWEEN HEARTBEATS | GLOBAL INDEX OF ANS FUNCTION |
| RMSSD (MS) | ROOT MEAN SQUARE OF SUCCESSIVE DIFFERENCES; CALCULATED THROUGH SQUARING THE INTERVALS BETWEEN HEARTBEATS | GLOBAL INDEX OF ANS FUNCTION |
| pNN50(%) | PROPORTION OF HEARTBEAT INTERVALS THAT DIFFER BY MORE THAN 50MS | INDICATIVE OF PARASYMPATHETIC ACTIVITY |
| NN50 | A COUNT VARIABLE; NUMBER OF PAIRS OF ADJACENT NN INTERVALS DIFFERING BY MORE THAN 50MS | INDICATIVE OF PARASYMPATHETIC ACTIVITY |
| STD HR (S) | STANDARD DEVIATION OF INSTANTANEOUS HEART RATE VALUES | GLOBAL INDEX OF ANS FUNCTION |
| *GEOMETRIC METHODS* | | |
| RR TRIANGULAR INDEX | TOTAL NUMBER OF ALL NN INTERVALS DIVIDED BY THE HEIGHT OF THE HISTOGRAM OF ALL NN INTERVALS MEASURED ON A DISCRETE SCALE (i.e. THE NUMBER OF ALL NN INTERVALS DIVIDED BY THE MAXIMUM OF THE DENSITY DISTRIBUTION) | GLOBAL INDEX OF ANS FUNCTION |
| TINN (MS) | BASELINE WIDTH OF THE DISTRIBUTION MEASURED AS A BASE OF A TRIANGLE, APPROXIMATING THE NN INTERVAL DISTRIBUTION | GLOBAL INDEX OF ANS FUNCTION |
| *FREQUENCY DOMAIN* | | |
| HF (MS$^2$) | POWER (MAGNITUDE) IN HIGH FREQUENCY RANGE, 0.15-0.4 HZ | INDEX OF PARASYMPATHETIC ACTIVITY ON HEART BASED ON RHYTHMIC RESPIRATION CYCLES |
| HFNU (%) | HF POWER IN NORMALIZED UNITS, AS A RATIO OF THE TOTAL POWER; [HF/(HF+LF)] X 100 | PROPORTION OF PARASYMPATHETIC ACTIVITY |
| LF (MS$^2$)* | POWER (MAGNITUDE) IN LOW FREQUENCY RANGE, 0.04-0.15Hz | MEASURE OF SYMPATHETIC AND/OR PARASYMPATHETIC ACTIVITY |
| LFNU (%)* | LF POWER IN NORMALIZED UNITS, AS A RATIO OF THE TOTAL POWER; [LF/(HF+ LF)] x 100 | MEASURE OF SYMPATHETIC AND/OR PARASYMPATHETIC ACTIVITY |
| LF/HF (MS$^2$)* | RATIO OF LOW FREQUENCY POWER TO HIGH FREQUENCY POWER | MEASURE OF SYMPATHETIC AND/OR PARASYMPATHETIC ACTIVITY |
| TOTAL POWER (MS$^2$) | VARIANCE OF ALL RR INTERVALS | OVERALL MAGNITUDE OF VARIABILITY WITHIN ANS; ABILITY OF ANS SYSTEM TO BE FLEXIBLE AND ADAPTABLE |

FIG. 4

| | CONTINUOUS WEARABLE MONITOR DATE | | | | | | | USER INPUT DATA | | | | | | | ANALYSIS DEVICE DATA | | | |
|---|---|---|---|---|---|---|---|---|---|---|---|---|---|---|---|---|---|---|
| HEART RATE VARIAB- ILITY (RMSSD) OR ANY FIG. 4 | DAY | PREVIOUS NIGHT SLEEP (HRS) | PREVIOUS NIGHT SLEEP QUALITY (1-10) | PREVIOUS DAY EXERSIZE /ACTIVITY LEVEL (1-10) | RESTING HEART RATE (BPM) | PREVIOUS DAY MAX HEART RATE | PREVIOUS DAY AVERAGE BODY TEMPERATURE E(F) | AGE | SEX (MALE/ FEMALE) | HEIGHT (FT) | WEIGHT (LBS) | CURRENT STRESS LEVEL (1-10) | ILLNESS (1-10) | MENST- RUATION (ON,OFF) | DRUG USE | DISEASE | ALTITUDE (FT) | WEATHER (DRY OR WET) | AMBIENT TEMPE- RATURE E(F) |
| 94 | 1 | 7 | 8 | 5 | 50 | 180 | 98.3 | 22 | FEMALE | 5'10" | 152 | 1 | 0 | OFF | ALBUTEROL | MILD ATHSMA | 1100 | DRY | 65 |
| 91 | 2 | 8 | 8 | 5 | 50 | 175 | 98.4 | 22 | FEMALE | 5'10" | 152 | 2 | 0 | OFF | NO | MILD ATHSMA | 1100 | DRY | 67 |
| 122 | 3 | 8 | 9 | 5 | 51 | 177 | 98.2 | 22 | FEMALE | 5'10" | 152 | 3 | 0 | OFF | NO | MILD ATHSMA | 1100 | DRY | 68 |
| 110 | 4 | 8 | 7 | 5 | 52 | 165 | 98.1 | 22 | FEMALE | 5'10" | 152 | 3 | 0 | OFF | ALBUTEROL | MILD ATHSMA | 1100 | DRY | 68 |
| 77 | 5 | 8 | 8 | 5 | 48 | 161 | 98.1 | 22 | FEMALE | 5'10" | 152 | 5 | 0 | OFF | ALBUTEROL | MILD ATHSMA | 1100 | DRY | 63 |
| 84 | 6 | 8 | 7 | 6 | 54 | 171 | 97.9 | 22 | FEMALE | 5'10" | 152 | 6 | 0 | OFF | ALBUTEROL | MILD ATHSMA | 300 | WET | 61 |
| 134 | 7 | 8 | 7 | 5 | 55 | 156 | 97.8 | 22 | FEMALE | 5'10" | 152 | 1 | 0 | OFF | ALBUTEROL | MILD ATHSMA | 300 | WET | 57 |
| 65 | 8 | 6 | 3 | 10 | 56 | 190 | 98.3 | 22 | FEMALE | 5'10" | 152 | 1 | 0 | OFF | NO | MILD ATHSMA | 1100 | DRY | 68 |
| 61 | 9 | 6 | 3 | 2 | 58 | 150 | 98.1 | 22 | FEMALE | 5'10" | 152 | 6 | 0 | OFF | ALBUTEROL | MILD ATHSMA | 1100 | DRY | 57 |
| 68 | 10 | 6 | 3 | 10 | 58 | 201 | 98.1 | 22 | FEMALE | 5'10" | 152 | 7 | 0 | OFF | ALBUTEROL | MILD ATHSMA | 1100 | DRY | 63 |
| 51 | 11 | 6 | 3 | 5 | 56 | 166 | 98.2 | 22 | FEMALE | 5'10" | 152 | 8 | 0 | OFF | NO | MILD ATHSMA | 1100 | DRY | 71 |
| 88 | 12 | 9 | 9 | 5 | 55 | 165 | 98 | 22 | FEMALE | 5'10" | 152 | 8 | 0 | OFF | ALBUTEROL | MILD ATHSMA | 1100 | DRY | 73 |
| 74 | 13 | 9 | 8 | 5 | 53 | 153 | 98 | 22 | FEMALE | 5'10" | 152 | 8 | 0 | OFF | ALBUTEROL | MILD ATHSMA | 1100 | DRY | 72 |
| 127 | 14 | 9 | 8 | 5 | 49 | 171 | 98.1 | 22 | FEMALE | 5'10" | 152 | 4 | 0 | OFF | NO | MILD ATHSMA | 1100 | DRY | 77 |
| 141 | 15 | 10 | 10 | 1 | 48 | 130 | 98 | 22 | FEMALE | 5'10" | 152 | 1 | 0 | OFF | NO | MILD ATHSMA | 1100 | DRY | 75 |
| 148 | 16 | 10 | 7 | 1 | 52 | 120 | 97.9 | 22 | FEMALE | 5'10" | 152 | 1 | 0 | ON | ALBUTEROL | MILD ATHSMA | 1100 | DRY | 71 |
| 131 | 17 | 8 | 6 | 5 | 53 | 144 | 97.6 | 22 | FEMALE | 5'10" | 152 | 0 | 0 | ON | ALBUTEROL | MILD ATHSMA | 1100 | WET | 66 |
| 147 | 18 | 8 | 8 | 5 | 51 | 165 | 98 | 22 | FEMALE | 5'10" | 152 | 0 | 0 | ON | ALBUTEROL | MILD ATHSMA | 1100 | WET | 63 |
| 79 | 19 | 8 | 10 | 5 | 54 | 164 | 98.1 | 22 | FEMALE | 5'10" | 152 | 3 | 0 | ON | ALBUTEROL | MILD ATHSMA | 1100 | WET | 63 |
| 73 | 20 | 4 | 3 | 8 | 55 | 177 | 98.3 | 22 | FEMALE | 5'10" | 152 | 1 | 5 | OFF | NO | MILD ATHSMA | 1100 | DRY | 77 |

HRV FINGERPRINT GENERATION DATA

FIG. 6

| Day | | | | | | Age | Sex | Height | Weight | | | Med | Condition | | Env | HRV |
|---|---|---|---|---|---|---|---|---|---|---|---|---|---|---|---|---|
| 21 | 8 | 8 | 7 | 56 | 164 | 98.2 | 22 | FEMALE | 5'10" | 152 | 1 | 5 | OFF | ALBUTEROL | MILD ATHSMA | 1100 | DRY | 75 |
| 22 | 8 | 9 | 6 | 54 | 180 | 98.1 | 22 | FEMALE | 5'10" | 152 | 4 | 5 | OFF | ALBUTEROL | MILD ATHSMA | 1100 | DRY | 70 |
| 23 | 6 | 5 | 5 | 55 | 183 | 98.1 | 22 | FEMALE | 5'10" | 152 | 5 | 8 | OFF | ALBUTEROL | MILD ATHSMA | 1100 | WET | 61 |
| 24 | 8 | 5 | 5 | 53 | 168 | 98.3 | 22 | FEMALE | 5'10" | 152 | 1 | 2 | OFF | ALBUTEROL | MILD ATHSMA | 1100 | DRY | 80 |
| 25 | 8 | 7 | 5 | 51 | 159 | 98 | 22 | FEMALE | 5'10" | 152 | 3 | 1 | OFF | NO | MILD ATHSMA | 1100 | DRY | 84 |
| 26 | 8 | 9 | 2 | 47 | 137 | 98 | 22 | FEMALE | 5'10" | 152 | 5 | 0 | OFF | NO | MILD ATHSMA | 1100 | DRY | 65 |
| 27 | 8 | 10 | 3 | 49 | 148 | 98.4 | 22 | FEMALE | 5'10" | 152 | 7 | 0 | OFF | ALBUTEROL | MILD ATHSMA | 1100 | DRY | 65 |
| 28 | 7 | 7 | 8 | 56 | 192 | 98 | 22 | FEMALE | 5'10" | 152 | 9 | 0 | OFF | ALBUTEROL | MILD ATHSMA | 1100 | DRY | 61 |
| 29 | 8 | 7 | 5 | 56 | 129 | 97.9 | 22 | FEMALE | 5'10" | 152 | 2 | 0 | OFF | ALBUTEROL | MILD ATHSMA | 1100 | DRY | 63 |
| 30 | 8 | 7 | 5 | 55 | 145 | 97.9 | 22 | FEMALE | 5'10" | 152 | 2 | 0 | OFF | ALBUTEROL | MILD ATHSMA | 1100 | DRY | 60 |
| 31 | 8 | 9 | 3 | 51 | 150 | 98.1 | 22 | FEMALE | 5'10" | 152 | 1 | 0 | OFF | ALBUTEROL | MILD ATHSMA | 1100 | DRY | 81 |

DAY 31 IMPACT (WHILE PLAYING A GAME OF PICKUP BASKETBALL THE SUBJECT SUFFERED A HEAD IMPACT BY BEING HIT BY ANOTHER PLAYER'S ELBOW)

CONCUSSION DIAGNOSIS AND RECOVERY DATA

| Day | | | | | | Age | Sex | Height | Weight | | | Med | Condition | | Env | HRV |
|---|---|---|---|---|---|---|---|---|---|---|---|---|---|---|---|---|
| 32 | 9 | 4 | 6 | 57 | 189 | 97.9 | 22 | FEMALE | 5'10" | 152 | 3 | 0 | OFF | ALBUTEROL | MILD ATHSMA | 1100 | DRY | 77 |
| 33 | 8 | 3 | 1 | 56 | 120 | 97.8 | 22 | FEMALE | 5'10" | 152 | 4 | 0 | OFF | NO | MILD ATHSMA | 1100 | DRY | 73 |
| 34 | 8 | 5 | 0 | 55 | 111 | 98.3 | 22 | FEMALE | 5'10" | 152 | 3 | 0 | OFF | ALBUTEROL | MILD ATHSMA | 1100 | DRY | 71 |
| 35 | 8 | 4 | 1 | 57 | 123 | 98.1 | 22 | FEMALE | 5'10" | 152 | 3 | 0 | OFF | ALBUTEROL | MILD ATHSMA | 1100 | DRY | 61 |
| 36 | 9 | 6 | 1 | 56 | 117 | 98.1 | 22 | FEMALE | 5'10" | 152 | 2 | 0 | OFF | NO | MILD ATHSMA | 1100 | DRY | 68 |
| 37 | 8 | 7 | 2 | 54 | 131 | 98.2 | 22 | FEMALE | 5'10" | 152 | 4 | 0 | OFF | NO | MILD ATHSMA | 1100 | DRY | 69 |
| 38 | 9 | 8 | 2 | 53 | 122 | 98 | 22 | FEMALE | 5'10" | 152 | 2 | 0 | OFF | ALBUTEROL | MILD ATHSMA | 1100 | DRY | 66 |
| 39 | 8 | 8 | 4 | 53 | 126 | 98.1 | 22 | FEMALE | 5'10" | 152 | 1 | 0 | OFF | ALBUTEROL | MILD ATHSMA | 1100 | DRY | 69 |
| 40 | 7 | 8 | 1 | 51 | 137 | 98.3 | 22 | FEMALE | 5'10" | 152 | 2 | 0 | OFF | NO | MILD ATHSMA | 1100 | DRY | 67 |

IN THE INITIAL 30 DAYS OF MONITORING ARE USED TO GENERATE THE SUBJECTS HRV FINGERPRINT. FOR EXAMPLE ON DAY 30 THE SUBJECT HAD SLEPT 8 HOURS THE NIGHT BEFORE, HAD A QUALITY NIGHT OF SLEEP, EXERCISED MODERATELY THE DAY BEFORE, HAD ALL NORMAL BIOMETRIC AND ENVIRONMENTAL DATA, AND HER HRV WAS 108. ON DAY 32, THE AFTER THE IMPACT, THE SUBJECT HAD NEARLY IDENTICAL VARIABLES. SHE SLEPT 8 HOURS, EXERCISED MODERATELY THE DAY BEFORE, HAD ALL NORMAL BIOMETRIC AND ENVIRONMENTAL DATA, ALTHOUGH SHE DID HAVE A POOR NIGHT OF SLEEP BUT THIS IS LIKELY DUE TO THE CONCUSSION. HOWEVER, ON THIS DAY HER HRV WAS 51. IT DOES NOT MATCH WHAT IT "SHOULD BE" AS PREDICTED BY HER HRV FINGERPRINT. HER FINGERPRINT WOULD PREDICT THAT HER HRV BE NEAR 100, AS IT WAS ON A NEARLY IDENTICAL DAY 31.

FIG. 6 (CONTINUED)

TRAUMATIC BRAIN INJURY DIAGNOSTICS SYSTEM AND METHOD

CROSS REFERENCE TO RELATED APPLICATIONS

This application claims priority to U.S. Provisional Patent Application No. 62/829,462, filed Apr. 4, 2019, which is hereby incorporated herein by reference in its entirety.

TECHNICAL FIELD

The present invention relates to a Traumatic Brain Injury (TBI) diagnostics system and method. More specifically, the present invention relates to TBI diagnostics by Heart Rate Variability Fingerprinting.

BACKGROUND

A concussion is a mild traumatic brain injury (mTBI) that affects brain function. Concussions and more severe TBI are generally caused by head trauma, such as hits or blows to the head, blast forces from explosions, and violent shaking of the head and/or upper body. mTBI are particularly common to players of contact sports and military combat personnel. Symptoms of a mTBI may last days, weeks, or longer. Symptoms may include headaches, head pressure, problems with concentration, memory, balance and/or coordination, temporary loss of consciousness, confusion or foggy feelings, amnesia surrounding the traumatic event, dizziness, ringing in the ears, nausea, vomiting, slurred speech, delayed responsiveness, appearing dazed, and/or fatigue, or any combination thereof mTBI may be temporary but may also lead to long term or permanent damage to the brain. Currently, mTBI may be diagnosed based on a variety of tests. For example, mTBI may be diagnosed based on symptom self-reporting. Post-Concussion Symptom Scale (PCSS) and Graded Symptom Checklist (GSC) are two of the most common scales used by medical professionals, but both are highly subjective. Neurological examinations (e.g., checking vision, hearing, strength, balance, coordination, and/or reflexes) are also used to diagnose mTBI. However, the most common neurological examination, the Balance Error Scoring System (BESS), has limitations as it is subjective and easily manipulated by the subject. Cognitive testing (e.g., testing memory, concentration, ability to recall information, processing speed) is used to diagnosed mTBI. However, these tests (most frequently ImPACT® testing and frequently kingdevick) have been heavily scrutinized in the scientific literature for lack of accuracy and validity. Imaging tests (e.g., cranial computerized tomography (CT) scan, magnetic resonance imaging (MRI)) and observation are also used to diagnose mTBI. Invasive techniques such as obtaining numerous blood samples to determine blood serum biomarker concentrations (such as, for example, protein S100b), may also be employed to diagnose mTBI. A need exists for an objective, accessible, accurate, reliable, non-invasive method of diagnosing TBI.

BRIEF SUMMARY OF THE INVENTION

According to an embodiment, a method for diagnosing traumatic brain injury (TBI) in a subject may include repeatedly measuring heart rate variability (HRV) in the subject and a plurality of HRV altering variables; calculating an HRV fingerprint based on the subject's measured HRV and the measured plurality of HRV altering variables; generating a predicted HRV of the subject based on the HRV fingerprint; and diagnosing a TBI in the subject when the measured HRV of the subject deviates from the predicted HRV of the subject.

According to an embodiment, repeatedly measuring the plurality of HRV altering variables comprises collecting data with a wearable device configured to continuously or intermittently measure biometric data from at least one of exercise metrics, sleep metrics, heartrate metrics, body temperature, ambient temperature, altitude, weather, age, sex, height, weight, cardiovascular fitness, stress, menstruation, drug use, alcohol use, disease, illness, previous HRV, and TBI history.

According to an embodiment, repeatedly measuring the plurality of HRV altering variables comprises collecting data with a wearable device configured to continuously or intermittently measure biometric data from at least exercise metrics, sleep metrics, cardiovascular fitness, and alcohol use.

According to an embodiment, the wearable device includes one or more of optical heart rate sensors, electronic heart rate sensors, blood pressure sensors (systolic and or diastolic), magnetic heart rate sensors, biometric sensors, or ambient sensors.

According to an embodiment, calculating the HRV fingerprint of the subject includes using a linear mixed-effect model of an interaction between the HRV and the HRV altering variables.

According to an embodiment, the HRV fingerprint represents how the subject's body and the subject's HRV respond to external stimuli.

According to an embodiment, the method may include monitoring TBI recovery of the subject.

According to an embodiment, the method may include alerting the subject of a TBI diagnosis.

According to an embodiment, a system for diagnosing traumatic brain injury (TBI) in a subject includes a processor, and a computer-readable storage medium storing instructions which, when executed by the processor, cause the processor to perform a method comprising: repeatedly measuring heart rate variability (HRV) in the subject and a plurality of HRV altering variables; calculating an HRV fingerprint based on the subject's measured HRV and the measured plurality of HRV altering variables; generating a predicted HRV of the subject based on the HRV fingerprint; and diagnosing a TBI in the subject when the measured HRV of the subject deviates from the predicted HRV of the subject.

According to an embodiment, repeatedly calculating the measured HRV comprises collecting data with a wearable device configured to continuously or intermittently measure biometric data from at least exercise metrics, sleep metrics, cardiovascular fitness, and alcohol use.

According to an embodiment, the wearable device comprises one or more of optical heart rate sensors, electronic heart rate sensors, blood pressure sensors, magnetic heart rate sensors, biometric sensors, or ambient sensors.

According to an embodiment, calculating the HRV fingerprint of the subject comprises using a linear mixed-effect model of an interaction between the HRV and the HRV altering variables.

According to an embodiment, the HRV fingerprint represents how the subject's body and the subject's HRV respond to external stimuli.

According to an embodiment, the predicted HRV is an expected value of the subject's HRV without a TBI.

According to an embodiment, a computer-readable storage medium stores instructions which, when executed by a computing device, cause the computing device to perform a method comprising: repeatedly measuring heart rate variability (HRV) in the subject and a plurality of HRV altering variables; calculating an HRV fingerprint based on the subject's measured HRV and the measured plurality of HRV altering variables; generating a predicted HRV of the subject based on the HRV fingerprint; and diagnosing a TBI in the subject when the measured HRV of the subject deviates from the predicted HRV of the subject.

According to an embodiment, repeatedly calculating the measured HRV comprises collecting data with a wearable device configured to continuously or intermittently measure biometric data from at least exercise metrics, sleep metrics, cardiovascular fitness, and alcohol use.

According to an embodiment, the wearable device comprises one or more of optical heart rate sensors, electronic heart rate sensors, blood pressure sensors, magnetic heart rate sensors, biometric sensors, or ambient sensors.

According to an embodiment, calculating the HRV fingerprint of the subject comprises using a linear mixed-effect model of an interaction between the HRV and the HRV altering variables.

According to an embodiment, the HRV fingerprint represents how the subject's body and the subject's HRV respond to external stimuli.

Additional features, advantages, and embodiments of the invention are set forth or apparent from consideration of the following detailed description, drawings and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

FIG. 3 illustrates a continuous heart rate variability monitor, according to an embodiment of the disclosure;

FIG. 4 illustrates a chart of heart rate variability data analysis equations, according to an embodiment of the disclosure;

FIG. 6 illustrates exemplary data used for TBI diagnosis using HRV fingerprinting, according to an embodiment of the disclosure;

DETAILED DESCRIPTION OF THE INVENTION

Figure 1:
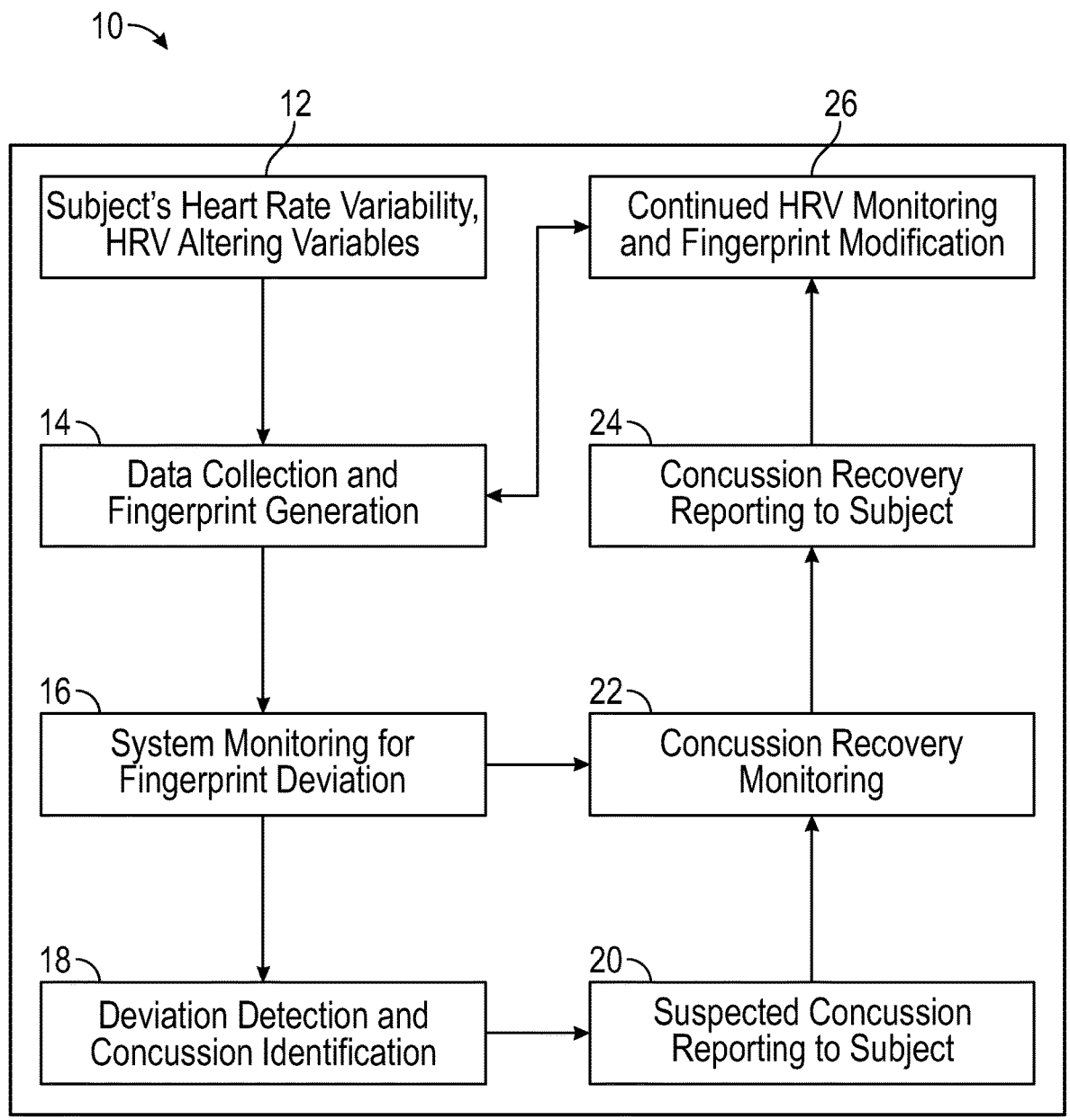
FIG. 1 illustrates a flow diagram for TBI diagnosis, according to an embodiment of the disclosure.

HRV is a well-documented biometric measurement of the difference in time between successive heartbeats. The HRV of a person (or subject) may change in response to a multitude of variables. For example, the HRV of the subject may change in response to, but not limited to, exercise metrics, sleep metrics, heartrate metrics, body temperature, ambient temperature, altitude, weather, age, sex, height, weight, cardiovascular fitness, stress, menstruation, drug use, alcohol use, disease, illness, previous HRV, etc., or combinations thereof. Research in the last two decades has found that HRV changes significantly following all severities of TBI, especially mTBI. Due to the degree that HRV may change because of these variables, the utility of HRV as a mTBI diagnostic tool has not been feasible, nor has it been discussed.

In several examples where HRV is measured in response to known concussion, matched controls are employed. The method of using matched controls is as follows. When the subject of interest suffers a head impact that may cause a concussion, an individual of roughly similar age, height, weight, and who has experienced similar exercise and sleep over the previous days as the subject, i.e. a teammate, is identified as the matched control. Together the HRV of the subject and the matched control are measured and compared. The comparison may then be used to approximate data about the subject's change in HRV from control but cannot be used to attempt to diagnose concussion in the subject. Although this method attempts to control for the aforementioned variables, it fails to do so because of the sensitivity of HRV to these variables. That is, a matched control may not accurately reflect the subject's individual changes in HRV in response to the aforementioned variables, and thus may not have the accuracy to diagnose concussion and/or monitor concussion recovery, in the subject. Furthermore, matched control methods may not be a clinically relevant model as the diagnosis of injury, illness, or disease is subject specific. That is, when diagnosing a broken arm for example, an X-ray of the subject's arm is taken and the break is compared to the unbroken bone that surrounds it, but a matched control is not typically used to identify if the arm is broken.

The present disclosure thus describes a TBI diagnosis system that uses the HRV of the subject to diagnose TBI. The term "traumatic brain injury (TBI)" is intended to encompass any type of traumatic brain injury, including a mild traumatic brain injury (mTBI) or concussion. Diagnosis of a TBI is done by repeatedly monitoring the subject's HRV and measuring directly and/or indirectly two or more of the aforementioned HRV altering variables to determine an HRV fingerprint of the subject. For example, this may mean direct measurement of max HR or indirect measurement of sleep type using HR as a proxy. An HRV fingerprint is the recording of sufficient HRV data on a subject to understand how the subject's body responds to external stimulus in order that future HRV may be predicted. External stimuli may include physical activity, consumption, environmental exposure and interactions, biological activity, etc. The HRV fingerprint may also represent how the subject's body and the subject's HRV respond to internal stimuli such as, for example, illness, menstruation, and past TBI. The HRV fingerprint is individual to the particular subject at that particular point in time, thus taking into account the aforementioned variables. The HRV fingerprint may accurately predict future heart rate variability, and may be used to calculated a predicted HRV. Deviation of the subject's measured HRV from the predicted heart rate variability may lead to an accurate diagnosis of TBI and/or diagnosis of TBI recovery in the subject.

The present disclosure describes a system for fingerprinting subject HRV and technique for TBI diagnostics using this HRV fingerprint. The system and method may include collection of information or data such as continuous collection of heartrates, HRV, and/or other identified data that affects HRV (e.g., exercise metrics, sleep metrics, heartrate metrics, body temperature, ambient temperature, altitude, weather, age, sex, height, weight, cardiovascular fitness, stress, menstruation, drug use, alcohol use, disease, illness, previous HRV, etc.). The collection of this data may be performed by monitoring, such as, for example, by a wearable monitor using optical, electronic, pressure (systolic and or diastolic), and/or magnetic sensor or sensors, or combinations thereof. Said sensors may be worn on any part or parts of the body that yields accurate and consistent biometric data (e.g., wrist, arm, neck, shoulder, head, torso, leg, etc.). Continuous collected data may be used to generate a once daily or multi-daily HRV score in the context of one or more HRV metrics as in FIG. 4. The one or more metrics may include exercise metrics, sleep metrics, heartrate metrics, body temperature, ambient temperature, altitude, weather, age, sex, height, weight, cardiovascular fitness, stress, menstruation, drug use, alcohol use, disease, illness, previous HRV, and/or other metrics that change human HRV, or combinations thereof. Several contextualized HRV scores (i.e., HRV scores measured against (measured in the context of) one or more of the aforementioned variables), may generate a subject's HRV fingerprint. The subject's HRV fingerprint may represent a normal, average, or ordinary HRV score (in the context of the one or more of the aforementioned variables) for the subject at a particular period of time. When the subject experiences head trauma, such as, for example, following head impact, the subject's measured HRV may be significantly deviated from an HRV that is predicted based on the HRV fingerprint, thus identifying a TBI in the subject. TBI recovery may be measured by a progression of the observed HRV score from the deviated score towards the normal, pre TBI HRV fingerprint.

The present disclosure describes heart rate variability fingerprint as a generated model to predict future HRV of the subject. The time needed to generate the HRV fingerprint is unknown. As more data is incorporated into the HRV fingerprint it continues to shift and update. That is, the longer the subject and/or the subject's surroundings are monitored, the more data is collected and incorporated into the HRV fingerprint. This allows the HRV fingerprint to be dynamic and change according to the subject (e.g., accounting for sleep, exercise, resting heartrate, max heartrate, body temperature, age, sex, height, weight, stress, illness, menstruation, drug use, disease, etc.) and the subject's surroundings (e.g., altitude, weather, ambient temperature), or any combination thereof.

Referring to FIG. 1, a TBI diagnosis flow diagram is shown. The flow diagram describes an exemplary method 10 for diagnosing a TBI in an individual or subject. At step 12, the person or subject's biometric heart rate variability is recorded. During step 12 the subject's HRV altering variables, e.g., heartrate, exercise, sleep, etc., are recorded directly and/or indirectly. For example, a direct measurement may be a direct measurement of max HR, while an indirect measurement may be a sleep type using HR as a proxy. Next, at step 14, data is continuously collected from step 12. The data may be the subject's heartrates, HRV, and/or other identified data that alters HRV (e.g., exercise metrics, sleep metrics, heartrate metrics, body temperature, ambient temperature, altitude, weather, age, sex, height, weight, cardiovascular fitness, stress, menstruation, drug use, alcohol use, disease, illness, previous HRV, etc.). This data may be recorded directly, e.g., max heartrate, resting heartrate, body temperature, ambient temperature, etc., or indirectly by means of biometric sensors and data processing for, e.g., cardiovascular load, sleep type, sleep duration, exercise duration, illness, menstruation, drug use, etc. The data may be collected by a monitoring device, such as, for example, by a wearable device or monitor, such as one from FIG. 3, using optical, electronic, pressure (systolic and or diastolic), and/or magnetic sensor or sensors, or combinations thereof. Additional monitors for contextualizing variables may be included, such as body temperature, ambient temperature, altitude, and/or other monitors, or combinations thereof. The data and/or monitoring may be continuous and real-time. That is, through the entirety of the method 10 of FIG. 1, data may be continuously monitored and/or collected by the monitoring device. Still at step 14, the data may be evaluated over a changing period of time to determine the subject's HRV fingerprint at that moment in time. As the monitoring is continuous, the monitoring of the heart rate may continue before, during, and after, the determination of the subject's HRV fingerprint. Additionally, the HRV fingerprint of the user may continuously shift as the predetermined period of time shifts. Thus, the HRV fingerprint may always account for the aforementioned variables as it may be modified as conditions of the subject change. Further continuous and real-time variable monitoring by external devices such as smartphones may be used to record contextualizing variables, as in, for example, the fingerprinting app illustrated in FIG. 5. In an embodiment, monitoring may continue for a predetermined time to result in an accurate HRV fingerprint. In an embodiment, this may be 30 days, although shorter (e.g., one day, one week, two weeks, etc.) or longer (e.g., 40 days, 45 days, 50 days, 60 days, etc.) time periods are contemplated. The HRV fingerprint may be calculated repeatedly from the data. In an embodiment, the HRV may be calculated as infrequently as once a day or once every two or three days. In an embodiment, the HRV fingerprint may be calculated as frequently as every minute or every hour or portion thereof.

At step 16, as the monitoring continues, any deviation from the HRV fingerprint determined in step 14 may be determined. Thus, in step 16, the system monitors for fingerprint deviation. The deviation above a predetermined threshold may indicate a TBI. When such a deviation is detected at step 18, a TBI may be diagnosed. At step 20, the TBI diagnosis is reported to the subject. This may be through a visual (e.g., illumination of mobile device or monitoring/sensor device), audio (e.g., announcement from mobile device or monitoring/sensor device), and/or physical (e.g., vibration of mobile device or vibration of monitoring device), and/or by other alert types or methods, or combinations thereof.

With continued reference to FIG. 1, step 22 evaluates the continuous monitoring to determine TBI recovery. As the HRV moves from the deviated value to the HRV fingerprint determined in step 14, recovery is monitored. At step 24, when the HRV reaches the HRV fingerprint determined in step 14, or within a predetermined range around the fingerprint, TBI recovery is reported to the subject. The reporting may be the same or similar to the reporting in step 20. After TBI recovery is reported, the method continues to monitor the HRV and determined if and when a deviation occurs at step 26. The window of time over which the fingerprint is calculated may move during the monitoring and a new or modified HRV fingerprint may be generated. The modified HRV fingerprint may replace or alter the fingerprint of step 14 and monitoring, reporting, and recovery of TBI may continue as previously described.

HRV fingerprint modification may occur as soon as the HRV fingerprint is initially generated. That is, the HRV fingerprint may be continuously updated. The HRV fingerprint may be continuously updated based on the subject monitoring and/or based on the environment or surroundings of the subject. The HRV fingerprint may be continuously updated before a TBI happens and after the TBI is recovered from, or any time therein.

Figure 2:
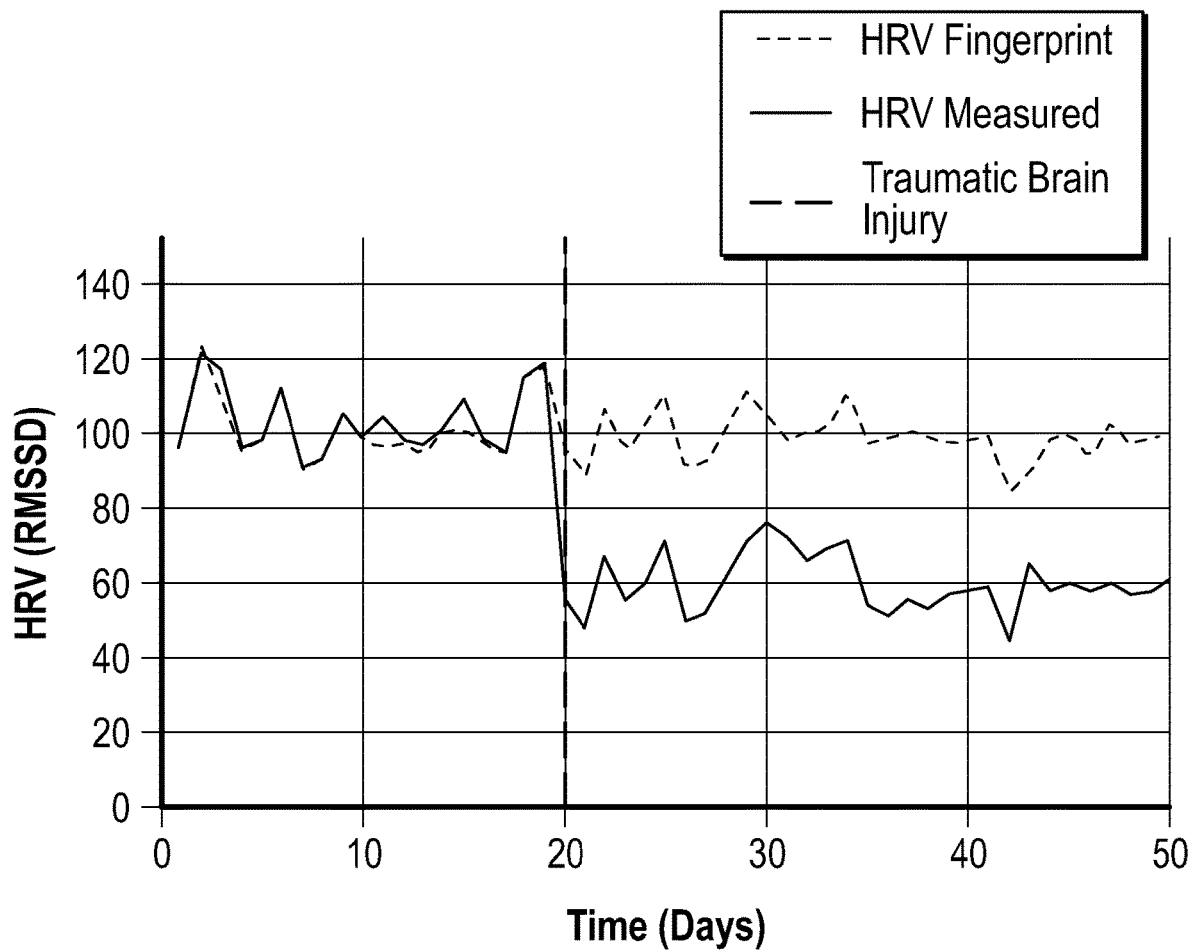
FIG. 2 illustrates an exemplary visualization of heart rate variability fingerprinting, which may be calculated using a mathematical model, against measured HRV before and after a traumatic brain injury, according to an embodiment of the disclosure.

Referring to FIG. 2, an exemplary visualization of HRV fingerprinting and post-impact HRV score is shown. As shown in FIG. 2, the HRV scores measured over time may be averaged or normalized (e.g., using Equation 1, Equation 2, or other mathematical model) to determine a HRV fingerprint of the subject. After a head trauma, the post-trauma HRV may be significantly deviated from the HRV fingerprint of the subject. This may be indicative of a TBI and TBI may be diagnosed.

Referring to FIG. 3, an exemplary wearable device for continuous HRV monitoring that may be used in the method of the present disclosure is shown. The wearable device may use a 932-MIKROE-3012 internal sensor or like sensor to measure HRV. This measurement tool may be worn on the wrist, arm, neck, shoulder, head, torso, or inserted into any clothing, padding, sports equipment, or military equipment. The measurement tool may be attached to the person and/or accessories or equipment using a clip system on the back of the device. The specific device in FIG. 3 is an example of the hardware, but is not an exclusive design needed for this method. By wearing this device, or other device that can measure and/or collect data that affect HRV, continuously or intermittently, the biometric data from exercise metrics, sleep metrics, heartrate metrics, body temperature, ambient temperature, altitude, weather, age, sex, height, weight, cardiovascular fitness, stress, menstruation, drug use, alcohol use, disease, illness, previous HRV, and other variables that affect HRV may be collected. The wearable devise may monitor continuously or not continuously (e.g., intermittently). The wearable device may include any electronic and/or magnetic device that measures heartrate and/or heartrate variability through any means including but not limited to optical heart rate sensors, electronic heart rate sensors, blood pressure sensors (systolic and or diastolic), magnetic heart rate sensors. The sensor may measure HRV through time, frequency, and or geometric domains, although root mean squared of the successive difference between R peaks (RMSSD) may be most reliable (FIG. 4).

Referring to FIG. 4, HRV calculation equations are shown. The equations may be used to measure or determine a HRV across seconds, minutes, hours, or days. One or more of the equations, separately or in concert, may be used to determine HRV.

One equation, Equation 1, may be a simplified theoretical linear mixed effects model (LMM) of the interaction between HRV altering variables to generate subject HRV fingerprint. LMM combines both population wide fixed effects, such as age, sex, height, weight, altitude, ambient temperature, weather, etc., with subject specific random effects, such as exercise metrics, sleep metrics, heartrate metrics, body temperature, cardiovascular fitness, stress, menstruation, drug use, alcohol use, disease, illness, previous HRV, etc. The formula for an LMM according to one aspect is: $Y_{ij} = X_{ij}\beta + Z_{ij}\gamma_i + \epsilon_{ij}$, where Y is HRV, i is a subject at time j, X are fixed effect HRV altering Variables, Z are random effect HRV altering Variables, and $\epsilon$ is the random error. Beta ($\beta$) of a variable represents the amount of influence a fixed effect variable has on predicting the HRV fingerprint, also called the variable's fixed effect coefficient. Gamma ($\gamma$) of a variable represents the amount of influence a random effect variable has on predicting the HRV fingerprint, also called the variable's random effect coefficient. In an LMM the covariance structure between the random effects and the covariance structure of the error term must be specified. The specification could include compound symmetric, autoregressive, unstructured, Toeplitz, variance components, AR(1), diagonal, or other specification.

Although several HRV altering variables are shown in Equation 1, only two or more may need be considered in determining HRV fingerprint.

$$\begin{aligned}
HRV_{ij} = &(\beta_0 + \gamma_{i0}) + \beta_1 ExerciseDuration_{ij} + \\
&\beta_2 ExerciseIntensity_{ij} + \beta_3 RestingHeartRate_{ij} + \\
&\beta_4 MaxHeartRate_{ij} + \beta_5 AverageHeartRate_{ij} + \\
&\beta_6 BodyTemperature_{ij} + \beta_7 AmbientTemperature_{ij} + \\
&\beta_8 Altitude_{ij} + \beta_9 Weather_{ij} + \beta_{10} Age_{ij} + \beta_{11} Sex_{ij} + \\
&\beta_{12} Height_{ij} + \beta_{13} Weight_{ij} + \\
&\beta_{14} CardiovascularFitness_{ij} + \beta_{15} Stress_{ij} + \\
&\beta_{16} Menstruation_{ij} + \beta_{17} DrugUse_{ij} + \\
&\beta_{18} Alcoholuse_{ij} + \beta_{19} Disease_{ij} + \beta_{20} Illness_{ij} + \\
&\beta_{21} PriorHRV_{ij} + \beta_{22} SleepEfficiency_{ij} + \\
&\beta_{23} SleepLatency_{ij} + \beta_{24} DeepSleepDuration_{ij} + \\
&\beta_{25} DeepSleepPercentage_{ij} + \\
&\beta_{26} LightSleepDuration_{ij} + \\
&\beta_{27} LightSleepPercentage_{ij} + \\
&\beta_{28} REMSleepDuration_{ij} + \\
&\beta_{29} REMSleepPercentage_{ij} + \\
&\beta_{30} NumberOfSleepDisturbances_{ij} + \\
&\beta_{31} SleepCycleConsistency_{ij} + \beta_{32} TimeInBed_{ij} + \\
&\beta_x OtherVariablesAlteringHRV_{ij} + \\
&\beta_{i1} ExerciseDuration_{ij} + \gamma_{i2} ExerciseIntensity_{ij} + \\
&\gamma_{i3} RestingHeartRate_{ij} + \gamma_{i4} MaxHeartRate_{ij} + \\
&\gamma_{i5} AverageHeartRate_{ij} + \gamma_{i6} BodyTemperature_{ij} + \\
&\gamma_{i7} AmbientTemperature_{ij} + \gamma_{i8} Altitude_{ij} + \\
&\gamma_{i9} Weather_{ij} + \gamma_{i10} Age_{ij} + \gamma_{i11} Sex_{ij} + \gamma_{i12} Height_{ij} + \gamma_{i13} Weight_{ij} + \gamma_{i14} CardiovascularFitness_{ij} + \\
&\gamma_{i15} Stress_{ij} + \gamma_{i16} Menstruation_{ij} + \gamma_{i17} DrugUse_{ij} + \\
&\gamma_{i18} Alcoholuse_{ij} + \gamma_{i19} Disease_{ij} + \gamma_{i20} Illness_{ij} + \\
&\gamma_{i21} PriorHRV_{ij} + \gamma_{i22} SleepEfficiency_{ij} + \\
&\gamma_{i23} SleepLatency_{ij} + \gamma_{i24} DeepSleepDuration_{ij} + \\
&\gamma_{i25} DeepSleepPercentage_{ij} + \\
&\gamma_{i26} LightSleepDuration_{ij} + \\
&\gamma_{i27} LightSleepPercentage_{ij} + \\
&\gamma_{i28} REMSleepDuration_{ij} + \\
&\gamma_{i29} REMSleepPercentage_{ij} + \\
&\gamma_{i30} NumberOfSleepDisturbances_{ij} + \\
&\gamma_{i31} SleepCycleConsistency_{ij} + \gamma_{i32} TimeInBed_{ij} + \\
&\gamma_{ix} OtherVariablesAlteringHRV_{ij} + \epsilon_{ij}
\end{aligned}$$

Equation 1

The mathematic equations from FIG. 4 show the different methods that HRV may be generated or calculated from a recording of heartbeats. Equation 1, on the other hand, is one potential way that this HRV may be predicted. In Equation 1, a collection of data (e.g., data on the subject and/or the subject's environment) may be employed to generate the HRV fingerprint. Referring to Equation 1, HRV is the output that may be predicted by the included contextualizing variables. Beta ($\beta$) of a variable represents the amount of influence a fixed effect variable has on predicting the HRV fingerprint, also called the variable's fixed effect coefficient. Gamma ($\gamma$) of a variable represents the amount of influence a random effect variable has on predicting the HRV fingerprint, also called the variable's random effect coefficient. E represents the error term. That is, $\epsilon$ represents an event that deviates from the collection of elements that affect HRV (i.e., a variable or event that is not a typical or expected elements that affect HRV). This may be, for example, the TBI event. Thus, the variables may represent known factors which affect HRV and the E may represent factors that may be uncommon (e.g., TBI) and/or unknown. Equation 1 represents a potential model that may be used to generate the HRV fingerprint, although alternative methods of generating or predicting the HRV fingerprint are contemplated.

Equation 1 considers a variety of variables that may change over the course of time or may be constant. Thus, as the subject changes (e.g., moves from rest to activity, moves from stress to relaxation, etc.), the variables that affect the HRV fingerprint may also change, thus changing the HRV fingerprint. For example, if the subject changes between states often, the HRV fingerprint maybe updated frequently and/or there may be a longer period of time of monitoring before determining the HRV fingerprint. Similarly, as the environment around the subject changes (e.g., weather changes, the subject travels between locations, etc.), the variables that affect the HRV fingerprint may also change, thus changing the HRV fingerprint. One may recognize that some variables may be static for longer periods (e.g., weight, height, age, menstruation, etc.) of time than others (e.g., activity, stress, exercise, heart rate, etc.). Additionally, some variables may remain constant (e.g., permanent disease, disorder or illness, sex, etc.). Thus, the HRV fingerprint may be ever changing and may continually be updated, as described in more detail to follow.

An application of the present TBI diagnostics system was assessed in the unpublished thesis by inventor Tristan Colaizzi, Williams College Honors Thesis in Psychology 2020. The study included over 150 Williams College Student-Athletes from six high risk sports teams: Men's Football, Men's Soccer, Women's Soccer, Men's Hockey, Women's Hockey, and Men's Rugby. Data was collected on Participant demographic information, and TBI was reported to the research team by Athletic Trainers, using current best practices for diagnosing and monitoring TBI. Participants wore wrist-based HR and HRV monitoring devices. From these devices we collected data on HRV and HRV altering variables including exercise metrics, sleep metrics, heartrate metrics, age, sex, height, weight, drug use, alcohol use, disease, illness, and previous HRV, among others. The present study calculated HRV using the Root Mean Squared of the Successive Difference in R to R peaks (RMSSD) as in FIG. 4. A similar simplified equation to Equation 1, Equation 2, was implemented in the present study to use collected HRV and HRV altering variables to calculate an individual's HRV fingerprint. This fingerprint was generated at the beginning of each day. The subject's HRV fingerprint was then compared against measured HRV as in FIG. 7 and FIG. 8. The term "measured HRV" is intended to indicate a measurement of variance in time between the beats of the subject's heart, as directly measured from the subject's heartbeat. The measured HRV may be measured by a wearable device, or by an ECG, for example.

One equation, Equation 2, is the applied linear mixed effects model of the interaction between HRV altering variables to generate subject HRV fingerprint. This Equation was used to calculate a subject's HRV fingerprint in the aforementioned study.

$$\log(HRV_{ij}) = (\beta_0 + \gamma_{0i}) + RHR_{ij}\beta_1 + HoS_{ij}\beta_2 + SE_{ij}\beta_3 + \epsilon_{ij} \quad \text{Equation 2}$$

The present exemplary model used implemented three HRV altering Variables: resting heart rate (RHR), hours of sleep (HoS), and sleep efficiency (SE). Sleep efficiency is defined as hours of sleep divided by hours in bed. The present model used random intercepts for each individual. The present model fit the log of HRV. The present model used a diagonal covariance structure for the random effects. The present model used an unstructured error covariance. Although the present example model had the above parameters, it could be fit using other parameters. The present example model could use other like models including, for example, a general linear model, another type of linear mixed model, a structural equation model, generalized estimating equations, etc.

Thus, referring back to the method of FIG. 1, the subject's actual HRV fingerprint may be determined from the continuous monitoring of the subject (e.g., from the data collected from a wearable device). A predicted or generated HRV may be calculated based on the aforementioned variables (e.g., variables of the subject and/or the subject's environment) by using the HRV fingerprint. The method described herein may compare the actual recorded HRV (referred to herein as "measured HRV") to the predicted HRV. When the deviation of the measured HRV from the predicted HRV is greater than a predetermined threshold (e.g., representing a significant deviation) a TBI may be diagnosed.

Figure 5:
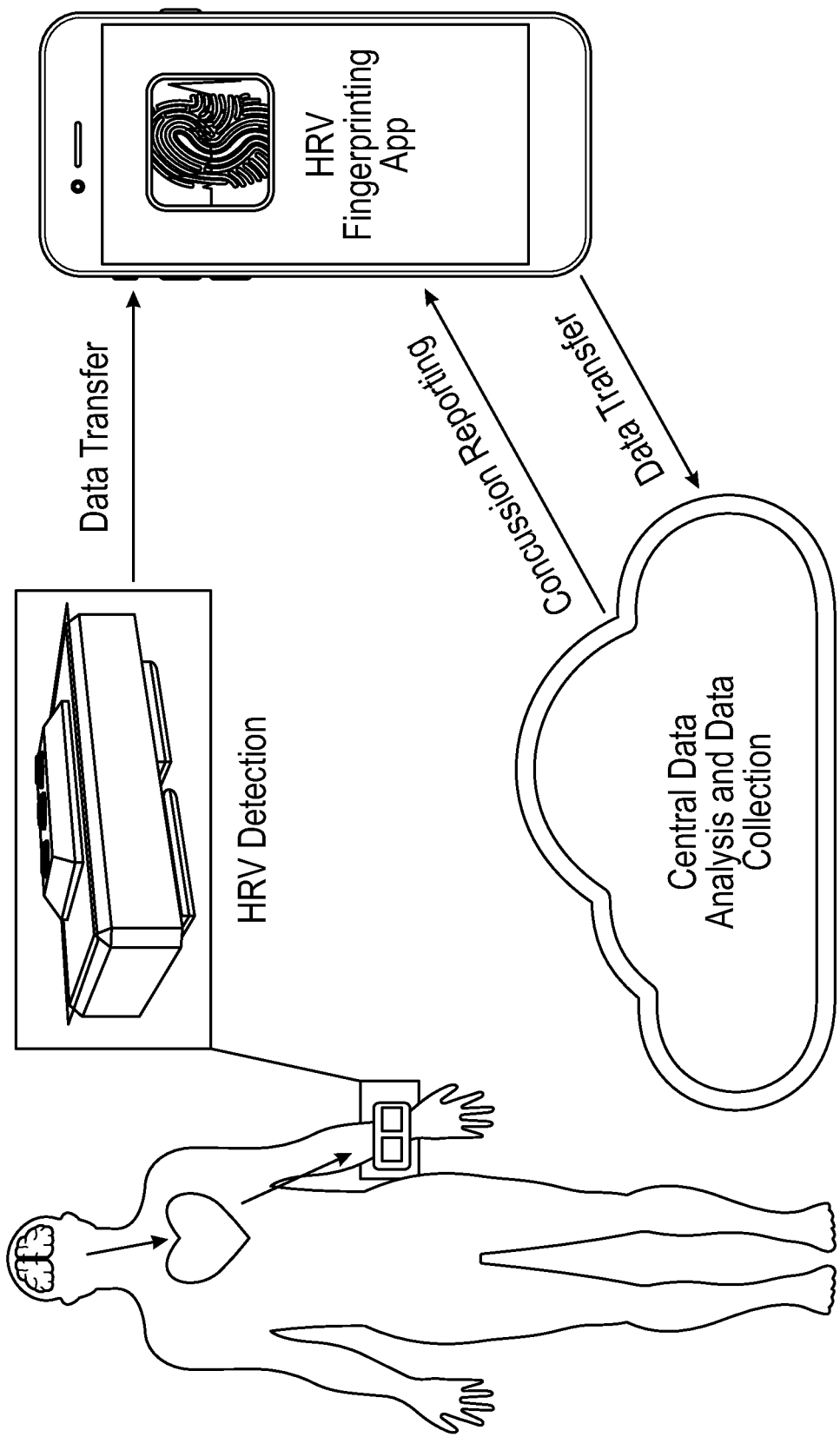
FIG. 5 illustrates a flow diagram for TBI diagnosis, according to an embodiment of the disclosure.

FIG. 5 shows a TBI diagnosis cloud diagram. As shown, the subject may have a wearable device, such as the exemplary device from FIG. 3. The wearable device may communicate with the subject's mobile device. The mobile device may include an HRV fingerprinting application. The application or "app" may communicate with the wearable device and/or a central server (e.g., cloud). The app may repeatedly determine the HRV fingerprint of the subject, compare the generated HRV, from the HRV fingerprint, to the measured HRV of the subject, determine when deviation has occurred, alert the subject of the current deviation, TBI diagnosis, TBI recovery, etc., as in FIG. 1. The app may also communicate with the central server or central data to retrieve information used for calculating the HRV contextualizing variables (e.g., altitude, weather, ambient temperature, etc.) and/or to communicate data to the central data for allowing the central server to compare and/or analyze the data and diagnose TBI. Referring to FIG. 6, an exemplary or hypothetical HRV fingerprinting and subsequent TBI diagnosis data chart is shown. The HRV fingerprinting may consider data from the continuous wearable monitoring, user input data (e.g., input into the app), and analysis device data (e.g., from the central data). As shown in FIG. 6, for example, the continuous wearable monitoring data may include the day, sleep hours, sleep quality, exercise, exercise intensity level, resting heart rate, max heart rate from the previous day, previous day average body temperature, or any like variable that alters HRV. The user input data may include age, sex, height, weight, current stress level, illness, menstruation, drug use, disease, or any like variable that alters HRV. The analysis device data may include altitude, weather, ambient temperature, or any like variable that alters HRV. Depending on sensor inclusion in the continuous wearable monitor, any of the aforementioned variables, or other variables that influence HRV, may be collected by the continuous wearable monitor.

In FIG. 6 the HRV fingerprint generation is modeled as being day 1 through day 30. The impact occurs on day 31, and days 32 through 40 are recovery. The subject has 30 initial days of monitoring that are used to generate the subject's HRV fingerprint, although this length of fingerprint generation is not fixed. For example, on day 30, the subject had slept 8 hours the night before, had a quality night of sleep, exercised moderately the day before, had all normal biometric and environmental data, and her HRV was 108. On day 32, the day after the impact, the subject had nearly identical variables. The subject slept 8 hours, exercised moderately the day before, had all normal biometric and environmental data, although the subject did have a poor night of sleep but this is likely due to the TBI. On this day the subject's HRV was 51. This does not match the predicted HRV for the subject. Based on the variables (e.g., measured from the wearable device and other variables) the subject's generated or predicted HRV fingerprint would be closer to 100. The exemplary or hypothetical HRV fingerprinting model uses a daily HRV measurement, and therefore TBI could be diagnosed the following day. As previously mentioned HRV could also, or instead, be collected on a second, minute, or hour basis, or fractions thereof. Under these more rapid measurements, TBI could be diagnosed as early as immediately after impact.

Figure 7:
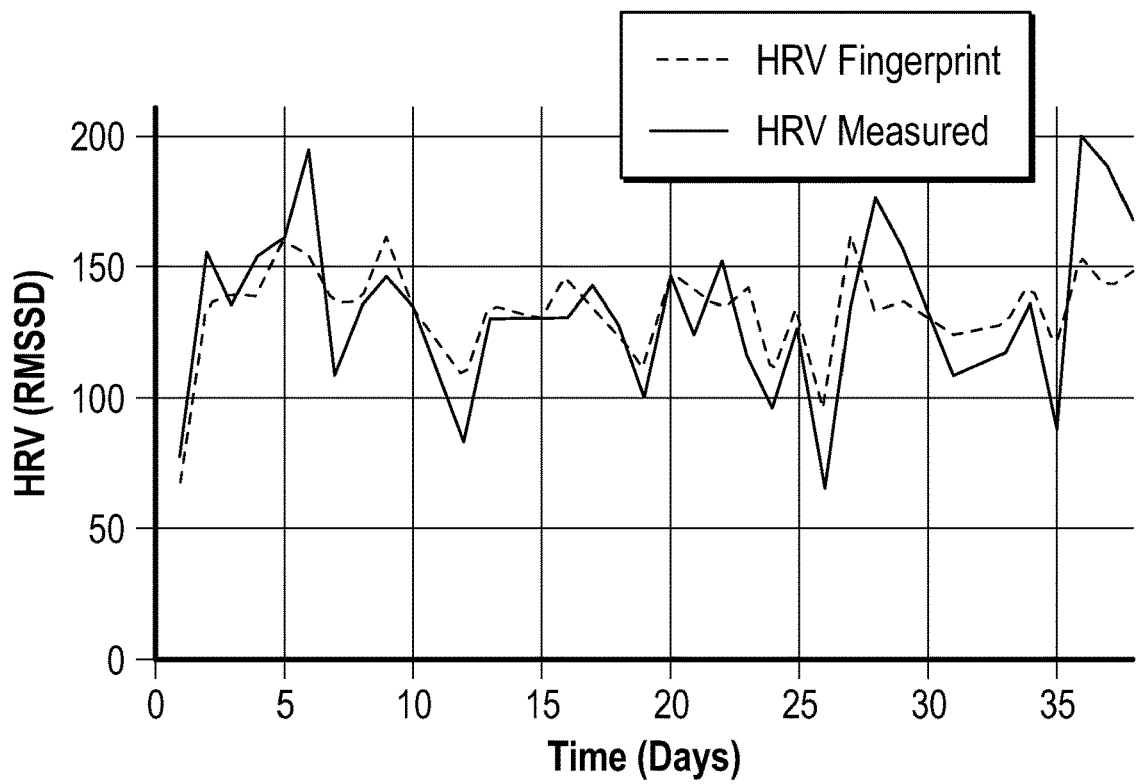
FIG. 7 illustrates a graphical representation of collected data and HRV fingerprinting modeling during the study of a control, no TBI, subject, according to an embodiment of the disclosure.

Referring to FIG. 7, an application of HRV fingerprinting to a control subject with no TBI. The daily generated HRV fingerprint is graphed against the daily measured HRV of the subject. The fit of HRV fingerprinting in predicting the measured HRV has an $r^2=0.77$, representing a strong model fit. This fit indicates that HRV fingerprinting, using HRV altering variables, is successful in predicting measured HRV. The present model, using Equation. 2, implements only three HRV altering variables, yet explains 77% of the variance in measured HRV. The inclusion of more HRV altering variables may improve upon this limited, simplified model and increase the percent variance explained, thus having a better model fit.

Figure 8:
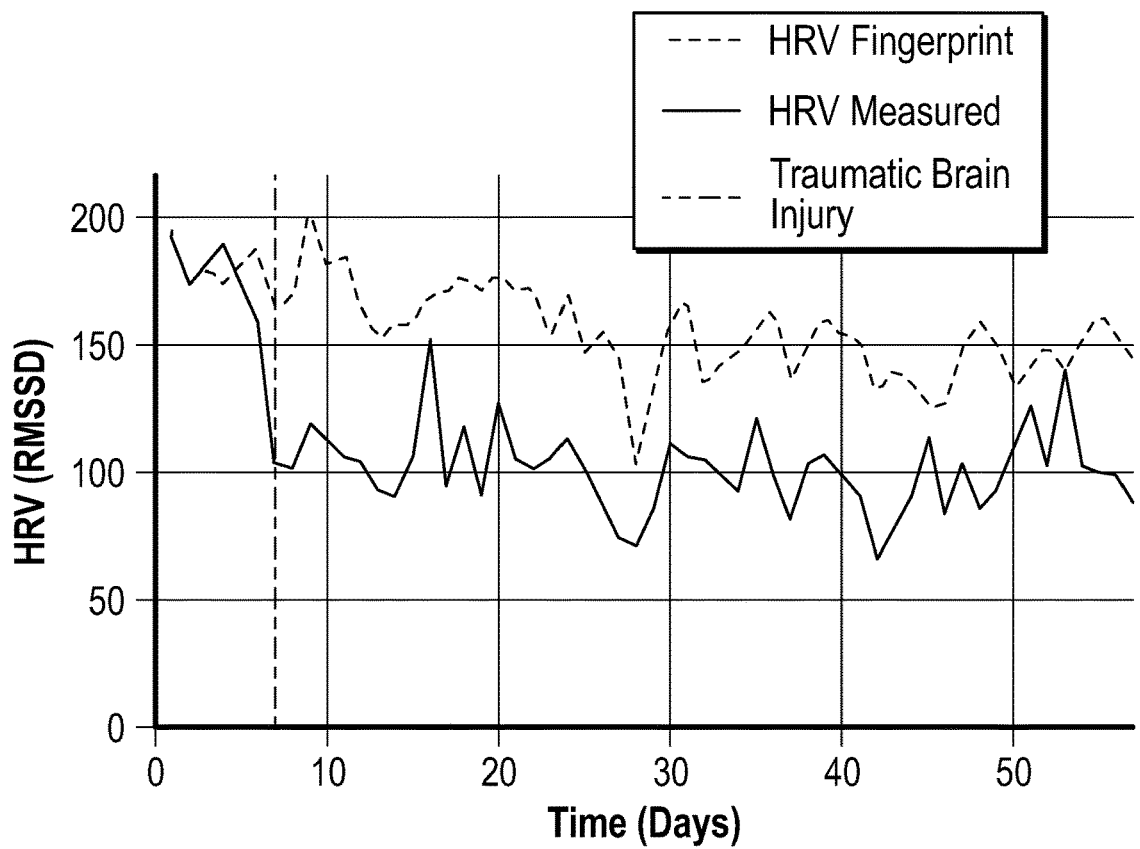
FIG. 8 illustrates a graphical representation of collected data and HRV fingerprinting modeling during the study of a confirmed TBI subject, according to an embodiment of the disclosure.

FIG. 8 shows an application of HRV fingerprinting in a subject that sustained a TBI. The subject sustained a TBI on day 7 in the graph. In the present exemplary graph, days prior to and after TBI were not continuous. Days 1-7 in FIG. 8 show high similarity in HRV fingerprint and measured HRV, indicating good model fit prior to TBI. Following TBI, as reported by Athletic Trainers on day 7 of the graph, the HRV fingerprint is consistently greater than measured HRV, indicating TBI. This difference may narrow after day 50 indicating recovery from TBI.

As described herein, the system and method of the present disclosure successfully controls for static and/or changing variables (e.g., exercise metrics, sleep metrics, heartrate metrics, body temperature, ambient temperature, altitude, weather, age, sex, height, weight, cardiovascular fitness, stress, menstruation, drug use, alcohol use, disease, illness, previous HRV, etc., or combinations thereof) in a subject by creating a HRV fingerprint of the subject. The HRV fingerprinting process works by continuously monitoring heart rate and/or HRV of the subject for an undetermined period of time (e.g., hours, days, weeks, months, years) to measure the degree to which an individual's HRV is changed by the variables. This measurement process is possible by the use of, for example, a 24/7 wearable device (e.g., FIG. 3) that allows for continuously, or non-continuous or intermittent, monitoring and/or collecting the biometric data from sleep, exercise, resting heartrate, max heartrate, body temperature, and other variables that affect HRV is collected. Additionally, altitude, weather, ambient temperature, and other external variables that affect HRV may be collected from the subject's device carrying the "HRV Fingerprinting App" (e.g., FIG. 5). Finally, user input of age, sex, height, weight, stress, illness, disease, menstruation, drug use, alcohol use, and other variables that affect HRV may be included for analysis and generation of the subject's HRV fingerprint. Depending on sensor inclusion in the continuous wearable monitor, any of the aforementioned variables, or other variables that influence HRV, may be collected by the continuous wearable monitor.

The measurement of one or more of these variables is measured against the changing HRV on a second, minute, hour, or daily basis of the subject. Using a linear mixed-effect model (Equation 1 and 2), or through a different analysis or mathematical modeling of this data, the subject's HRV fingerprint can be generated (FIG. 2). Such models may include, linear mixed-effect model, multiple regression model, general linear model, other types of linear mixed model, structural equation model, generalized estimating equations, or other mathematical model of an interaction between HRV and HRV altering variables. The subject's HRV fingerprint is unique and may only be generated through collection of data points. Once a subject's HRV fingerprint has been generated, future data points can be checked against it for deviation (FIG. 1). At this point, if a data point is recorded measurably different from the subject's HRV fingerprint a concussive event can be identified. This is possible because, following head impact while the device is still being continuously worn, the HRV of the subject will be measurably different than their HRV fingerprint would predict. This process can therefore diagnose a TBI by identifying an otherwise unexplained markedly different HRV score.

Additionally, the method may measure a subject's recovery following a TBI. After a TBI, HRV is not changed only for a single day, but may remain measurably different as the brain heals. Therefore, so long as the HRV continues to be measurably different from the expected HRV, derived from the subject's HRV fingerprint, the subject may still be concussed. When the observed HRV of a subject begins to move towards their expected HRV their recovery may be measured. Finally, when the subject's observed HRV matched their expected HRV, in the days, weeks months, or years following the initial impact, it may be concluded that the individual is no longer measurably concussed or has a TBI.

The HRV score used in this method may be generated using any one or more of the equations from FIG. 4, although RMSSD and HF may be preferred. A hypothetical example of a subject's data is included in FIG. 6. The structure and analysis of this data are an example, however this method may use many different data collection and analysis schemes. FIG. 6 outlines the hypothetical degree to which HRV is changed by TBI from the expected HRV that is generated by the HRV fingerprint. This hypothetical uses daily measured HRV, although data may be measured every minute, hour, day, week, month, year, etc. As the HRV fingerprint continues to improve with further data collection (FIG. 1, step 26) the sensitivity to smaller changes in HRV may be detected, minimizing the measurable HRV depression. The degree to which a change in HRV is measurable has not yet been determined, although any deviation in HRV that is unexplained by the subjects HRV fingerprint is potentially measurable.

The system and method described herein may be employed in sports TBI diagnostics. Alternatively, or additionally, the system and method may also diagnose TBI in non-sports situations. For example, data may be collected by the wearable device in a similar manner to conventional fitness trackers, smartwatches, heart rate trackers, body trackers, sleep trackers, and/or other wearable devices that monitor a subject. This would include athletes, civilians, and military personnel in all capacities and situations.

According to some embodiments, a system for diagnosing TBI in a subject includes a processor, and a computer-readable storage medium storing instructions which, when executed by the processor, cause the processor to perform the methods described herein.

Figure 9:
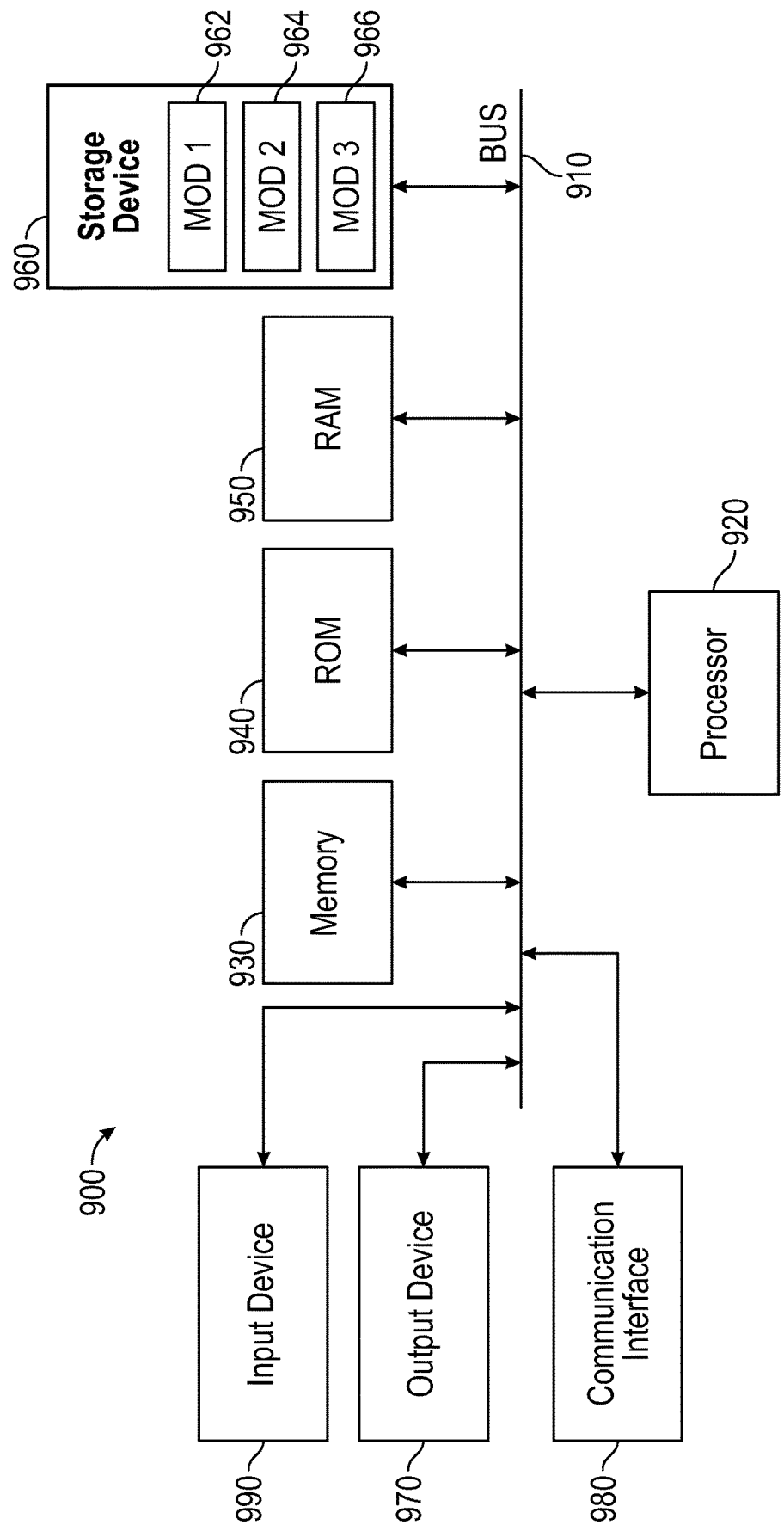
FIG. 9 illustrates an example system for diagnosing TBI in a subject, according to an embodiment of the disclosure.

With reference to FIG. 9, an example system may include a general-purpose computing device 900, including a processing unit (CPU or processor) 920 and a system bus 910 that couples various system components including the system memory 930 such as read-only memory (ROM) 940 and random access memory (RAM) 950 to the processor 920. The system 900 can include a cache of high-speed memory connected directly with, in close proximity to, or integrated as part of the processor 920. The system 900 copies data from the memory 930 and/or the storage device 960 to the cache for quick access by the processor 920. In this way, the cache provides a performance boost that avoids processor 920 delays while waiting for data. These and other modules can control or be configured to control the processor 920 to perform various actions. Other system memory 930 may be available for use as well. The memory 930 can include multiple different types of memory with different performance characteristics. It can be appreciated that the disclosure may operate on a computing device 900 with more than one processor 920 or on a group or cluster of computing devices networked together to provide greater processing capability. The processor 920 can include any general purpose processor and a hardware module or software module, such as module 1 962, module 2 964, and module 3 966 stored in storage device 960, configured to control the processor 920 as well as a special-purpose processor where software instructions are incorporated into the actual processor design. The processor 920 may essentially be a completely self-contained computing system, containing multiple cores or processors, a bus, memory controller, cache, etc. A multi-core processor may be symmetric or asymmetric.

The system bus 910 may be any of several types of bus structures including a memory bus or memory controller, a peripheral bus, and a local bus using any of a variety of bus architectures. A basic input/output (BIOS) stored in ROM 940 or the like, may provide the basic routine that helps to transfer information between elements within the computing device 900, such as during start-up. The computing device 900 further includes storage devices 960 such as a hard disk drive, a magnetic disk drive, an optical disk drive, tape drive or the like. The storage device 960 can include software modules 962, 964, 966 for controlling the processor 920. Other hardware or software modules are contemplated. The storage device 960 is connected to the system bus 910 by a drive interface. The drives and the associated computer-readable storage media provide nonvolatile storage of computer-readable instructions, data structures, program modules and other data for the computing device 900. In one aspect, a hardware module that performs a particular function includes the software component stored in a tangible computer-readable storage medium in connection with the necessary hardware components, such as the processor 920, bus 910, display 970, and so forth, to carry out the function.

In another aspect, the system for diagnosing TBI in a subject can use a processor and computer-readable storage medium to store instructions which, when executed by the processor, cause the processor to perform a method or other specific actions. The basic components and appropriate variations are contemplated depending on the type of device, such as whether the device 900 is a small, handheld computing device, a desktop computer, or a computer server.

Although the exemplary embodiment described herein employs the hard disk 960, other types of computer-readable media which can store data that are accessible by a computer, such as magnetic cassettes, flash memory cards, digital versatile disks, cartridges, random access memories (RAMs) 950, and read-only memory (ROM) 940, may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with the computing device 900, an input device 990 represents any number of input mechanisms, such as a microphone for speech, a touch-sensitive screen for gesture or graphical input, keyboard, mouse, wrist watch or other wearable device, motion input, speech and so forth. An output device 970 can also be one or more of a number of output mechanisms known to those of skill in the art. In some instances, multimodal systems enable a user to provide multiple types of input to communicate with the computing device 900. The communications interface 980 generally governs and manages the user input and system output. There is no restriction on operating on any particular hardware arrangement and therefore the basic features here may easily be substituted for improved hardware or firmware arrangements as they are developed.

The system for diagnosing TBI in a subject can use a processor and computer-readable storage medium to store instructions which, when executed by the processor, cause the processor to perform a method including repeatedly measuring heart rate variability (HRV) in the subject and a plurality of HRV altering variables; calculating an HRV fingerprint based on the subject's measured HRV and the measured plurality of HRV altering variables; generating a predicted HRV of the subject based on the HRV fingerprint; and diagnosing a TBI in the subject when the measured HRV of the subject deviates from the predicted HRV of the subject. Repeatedly measuring the plurality of HRV altering variables may include collecting data with a wearable device configured to continuously or intermittently measure biometric data from at least exercise metrics, sleep metrics, cardiovascular fitness, and alcohol use.

The wearable device may include one or more of optical heart rate sensors, electronic heart rate sensors, blood pressure sensors, magnetic heart rate sensors, biometric sensors, or ambient sensors. Calculating the HRV fingerprint of the subject may include using a linear mixed-effect model of an interaction between HRV and HRV altering variables. The HRV fingerprint may represent how the subject's body and the subject's HRV respond to external stimuli. The method may include monitoring TBI recovery of the subject, and alerting the subject of a TBI diagnosis.

According to some aspects of the invention, a computer-readable storage medium stores instructions which, when executed by a computing device, cause the computing device to perform a method including repeatedly measuring heart rate variability (HRV) in the subject and a plurality of HRV altering variables; calculating an HRV fingerprint based on the subject's measured HRV and the measured plurality of HRV altering variables; generating a predicted HRV of the subject based on the HRV fingerprint; and diagnosing a TBI in the subject when the measured HRV of the subject deviates from the predicted HRV of the subject.

Repeatedly calculating the measured HRV may include collecting data with a wearable device configured to continuously or intermittently measure biometric data from at least exercise metrics, sleep metrics, cardiovascular fitness, and alcohol use. The wearable device comprises one or more of optical heart rate sensors, electronic heart rate sensors, blood pressure sensors, magnetic heart rate sensors, biometric sensors, or ambient sensors. Calculating the HRV fingerprint of the subject may include using a linear mixed-effect model of an interaction between the HRV and the HRV altering variables. The HRV fingerprint may represent how the subject's body and the subject's HRV respond to external stimuli.

Only exemplary embodiments of the present invention and but a few examples of its versatility are shown and described in the present disclosure. It is to be understood that the present invention is capable of use in various other combinations and environments and is capable of changes or modifications within the scope of the inventive concept as expressed herein.

Although the foregoing description is directed to the preferred embodiments of the invention, it is noted that other variations and modifications will be apparent to those skilled in the art, and may be made without departing from the spirit or scope of the invention. Moreover, features described in connection with one embodiment of the invention may be used in conjunction with other embodiments, even if not explicitly stated above.

The invention claimed is:

1. A method for diagnosing traumatic brain injury (TBI) in a subject, the method comprising:
   repeatedly measuring heart rate variability (HRV) in the subject to generate a measured HRV;
   repeatedly measuring a plurality of HRV altering variables in the subject, the plurality of HRV altering variables including heartrate metrics, sleep metrics, and exercise metrics;
   calculating an HRV fingerprint based on the measured HRV and the plurality of HRV altering variables over a predetermined window of time;
   generating a calculated HRV of the subject based on the HRV fingerprint for the predetermined window of time;
   measuring a real-time HRV;
   comparing the real-time HRV with the calculated HRV; and
   diagnosing a TBI in the subject when the real-time HRV of the subject is outside a computed range from the calculated HRV of the subject,
   wherein the predetermined window of time over which the HRV fingerprint is calculated moves resulting in a modified HRV fingerprint from which a modified calculated HRV is generated, the diagnosing of the TBI occurring when the real-time HRV is outside a computed range from the calculated HRV or the modified calculated HRV.

2. The method of claim 1, wherein repeatedly measuring the plurality of HRV altering variables comprises collecting data with a wearable device configured to continuously or intermittently measure biometric data from at least one of exercise metrics, sleep metrics, heartrate metrics, body temperature, ambient temperature, altitude, weather, age, sex, height, weight, cardiovascular fitness, stress, menstruation, drug use, alcohol use, disease, illness, previous HRV, and TBI history.

3. The method of claim 1, wherein repeatedly measuring the plurality of HRV altering variables comprises collecting data with a wearable device configured to continuously or intermittently measure biometric data from at least exercise metrics, sleep metrics, cardiovascular fitness, and alcohol use.

4. The method of claim 3, wherein the wearable device comprises one or more of optical heart rate sensors, electronic heart rate sensors, blood pressure sensors, magnetic heart rate sensors, biometric sensors, or ambient sensors.

5. The method of claim 1, wherein calculating the HRV fingerprint of the subject comprises using a linear mixed-effect model of an interaction between the HRV and the HRV altering variables.

6. The method of claim 1, wherein the HRV fingerprint represents how the subject's body and the subject's HRV respond to external stimuli.

7. The method of claim 1, wherein the calculated HRV is an expected value of the subject's HRV without a TBI.

8. The method of claim 1, further comprising, monitoring TBI recovery of the subject by:
   continuing to calculate the HRV fingerprint of the subject;
   continuing to generate the calculated HRV of the subject based on the HRV fingerprint;
   continuing to compare the calculated HRV with the measured HRV; and
   monitoring the recovery from TBI in the subject when the measured HRV of the subject becomes more similar to the calculated HRV, or is within the computed range of the calculated HRV.

9. The method of claim 1, further comprising alerting the subject of a TBI diagnosis.

10. A system for diagnosing traumatic brain injury (TBI) in a subject, the system comprising:
    a processor; and
    a computer-readable storage medium storing instructions which, when executed by the processor, cause the processor to perform a method comprising:
       repeatedly measuring heart rate variability (HRV) in the subject to generate a measured HRV;
       repeatedly measuring a plurality of HRV altering variables in the subject, the plurality of HRV altering variables including heartrate metrics, sleep metrics, and exercise metrics;
       calculating an HRV fingerprint based on the measured HRV and the plurality of HRV altering variables over a predetermined window of time;
       generating a calculated HRV of the subject based on the HRV fingerprint for the predetermined window of time;
       measuring a real-time HRV;
       comparing the real-time HRV with the calculated HRV; and
       diagnosing a TBI in the subject when the real-time HRV of the subject is outside a computed range from the calculated HRV of the subject,
       wherein the predetermined window of time over which the HRV fingerprint is calculated moves resulting in a modified HRV fingerprint from which a modified calculated HRV is generated, the diagnosing of the TBI occurring when the real-time HRV is outside a computed range from the calculated HRV or the modified calculated HRV.

11. The system of claim 10, wherein repeatedly calculating the measured HRV comprises collecting data with a wearable device configured to continuously or intermittently measure biometric data from at least exercise metrics, sleep metrics, cardiovascular fitness, and alcohol use.

12. The system of claim 11, wherein the wearable device comprises one or more of optical heart rate sensors, electronic heart rate sensors, blood pressure sensors, magnetic heart rate sensors, biometric sensors, or ambient sensors.

13. The system of claim 10, wherein calculating the HRV fingerprint of the subject comprises using a linear mixed-effect model of an interaction between the HRV and the HRV altering variables.

14. The system of claim 10, wherein the HRV fingerprint represents how the subject's body and the subject's HRV respond to external stimuli.

15. The system of claim 10, wherein the calculated HRV is an expected value of the subject's HRV without a TBI.

16. A tangible computer-readable storage medium storing instructions which, when executed by a computing device, cause the computing device to perform a method comprising:

repeatedly measuring heart rate variability (HRV) in the subject to generate a measured HRV;

repeatedly measuring a plurality of HRV altering variables in the subject, the plurality of HRV altering variables including heartrate metrics, sleep metrics, and exercise metrics;

calculating an HRV fingerprint based on the measured HRV and the plurality of HRV altering variables over a predetermined window of time;

generating a calculated HRV of the subject based on the HRV fingerprint for the predetermined window of time;

measuring a real-time HRV;

comparing the real-time HRV with the calculated HRV; and diagnosing a TBI in the subject when the real-time HRV of the subject is outside a computed range from the calculated HRV of the subject, wherein the predetermined window of time over which the HRV fingerprint is calculated moves resulting in a modified HRV fingerprint from which a modified calculated HRV is generated, the diagnosing of the TBI occurring when the real-time HRV is outside a computed range from the calculated HRV or the modified calculated HRV.

17. The computer-readable storage medium of claim 16, wherein repeatedly calculating the measured HRV comprises collecting data with a wearable device configured to continuously or intermittently measure biometric data from at least exercise metrics, sleep metrics, cardiovascular fitness, and alcohol use.

18. The computer-readable storage medium of claim 17, wherein the wearable device comprises one or more of optical heart rate sensors, electronic heart rate sensors, blood pressure sensors, magnetic heart rate sensors, biometric sensors, or ambient sensors.

19. The computer-readable storage medium of claim 16, wherein calculating the HRV fingerprint of the subject comprises using a linear mixed-effect model of an interaction between the HRV and the HRV altering variables.

20. The computer-readable storage medium of claim 16, wherein the HRV fingerprint represents how the subject's body and the subject's HRV respond to external stimuli.

\* \* \* \* \*